(12) United States Patent
Rosenberg

(10) Patent No.: US 6,465,521 B1
(45) Date of Patent: Oct. 15, 2002

(54) COMPOSITION FOR DESORBING BACTERIA

(75) Inventor: Melvyn Rosenberg, Ramat-Gan (IL)

(73) Assignee: Ramot University Authority for Applied Research & Industrial Development, Ltd. (IL)

( * ) Notice: Subject to any disclaimer, the term of this patent is extended or adjusted under 35 U.S.C. 154(b) by 0 days.

(21) Appl. No.: 08/178,353

(22) Filed: Jan. 6, 1994

Related U.S. Application Data

(63) Continuation of application No. 07/330,262, filed on Mar. 29, 1989, now abandoned.

(30) Foreign Application Priority Data

Mar. 30, 1988 (IL) .................................. 85934

(51) Int. Cl.$^7$ .................... A61K 31/14; A61K 31/44; A61K 31/155; A61K 7/18
(52) U.S. Cl. .................. 514/642; 514/643; 514/358; 514/635; 424/52; 424/54
(58) Field of Search ................ 514/642, 358, 514/635; 424/52, 54

(56) References Cited

U.S. PATENT DOCUMENTS

| | | | | |
|---|---|---|---|---|
| 3,277,118 A | * | 10/1966 | Schmid et al. ................ | 424/52 |
| 4,123,512 A | * | 10/1978 | Gaffar ......................... | 424/52 |
| 4,292,304 A | * | 9/1981 | Barels et al. ................. | 424/52 |
| 4,442,125 A | * | 4/1984 | Thiele ......................... | 514/60 |
| 4,525,342 A | * | 6/1985 | Weiss et al. | |
| 4,693,888 A | * | 9/1987 | Miyahana et al. ........... | 424/49 |

OTHER PUBLICATIONS

Stueber et al 1987 CA106:29939f.*
McCutcheon's Detergents & Emulsifiers 1971 Annual Allured Publishing Corp. p. 2,30,42.*
CA91:44413v Henyog et al.*
CA93:192041d Kumar et al (chlorhexidine etc.).*
CA95:30423u Oral Compositions with Stabilized Tin Salts (mouthwashs, amines & quatz), amine fluoride) Muehlemann et al,.*
CA 108:81855f Pianotti, R.S. (chlorhexidine in mouthwash).*
CA95:156499s Gaffar et al. (catylpyridihium chloride).*
CA99:191566r Gehring, F. (amine & NaF).*
CA101:197959c Weiss et al. (oil & $H_2O$ bacteria removal).*
CA101:137044v Bilton, G.L, (oil, water, emulifier).*

* cited by examiner

Primary Examiner—Russell Travers
(74) Attorney, Agent, or Firm—Hoffman, Wasson & Gitler, PC

(57) ABSTRACT

The invention provides a composition for desorbing bacteria from solid surfaces and from living tissues, which is in the form of a two-phase preparation, and which upon shaking forms a temporary oil-in-water emulsion of limited lifetime, the composition comprising:

a) about 50 to about 97% w/w of an aqueous phase;
b) about 3 to about 50% w/w of a water immiscible oily phase, comprising a vegetable oil, a mineral oil, a pharmacologically acceptable aliphatic hydrocarbon or a mixture thereof; and
c) about 0.003 to about 2.0% w/w of an amphipathic cationic moiety in an effective amount to enable the formation of the temporary oil-in-water emulsion which emulsion breaks down and separates within a period of about 10 seconds to thirty minutes of the formation thereof.

13 Claims, No Drawings

COMPOSITION FOR DESORBING BACTERIA

This application is a continuation, of application Ser. No. 07/330,262 filed Mar. 29, 1989, now abandoned.

The present invention relates to novel compositions which desorb bacteria and other microorganisms from solid surfaces and from living tissue.

The main use contemplated for the compositions of the present invention is in oral hygiene. Compositions of the invention can also be used in entirely different applications, where microorganisms are to be removed from surfaces to which they are attached, or where enhanced microbial adhesion to oil droplets is desired.

According to the present invention there is now provided a composition for desorbing bacteria from solid surfaces and from living tissues, which is in the form of a two-phase preparation, and which upon shaking forms a temporary oil-in-water emulsion of limited lifetime said composition comprising:

a) about 50 to about 97% w/w of an aqueous phase;
b) about 3 to about 50% w/w of a water immiscible oily phase, comprising a vegetable oil, a mineral oil, a pharmacologically acceptable aliphatic hydrocarbon or a mixture thereof; and
c) about 0.003 to about 2.0% w/w of an amphipathic cationic moiety in an effective amount to enable the formation of said temporary oil-in-water emulsion which emulsion breaks down and separates within a period of about 10 seconds to thirty minutes of the formation thereof.

Amongst edible oils, which can be used to form said water immiscible oily phase there may be mentioned oils such as olive oil, corn oil, coconut oil, soybean oil, safflower oil. There can also be used a wide variety of pharmacologically acceptable hydrocabons such as octane, decane, tetradecane, hexadecane, xylene, white mineral oil, and mixtures thereof etc.

Amongst suitable colors, there may be mentioned colors of triphenylmethane, naphthol, xanthene, monoazo, pyrazol, anthraquinone and cationic colors; examples include Food Blue 2 and its ammonium salt; D&C Yellow No. 7, D&C Yellow No. 10, D&C Yellow Nos. 4, 6, 22, 28, 33 or 40; D&C Green No. 5, D&C Orange No. 11, D&C Red Nos. 19 and 37, Basic Blue Nos. 6, 9, 41, 99, etc.

Preferably said amphipathic cationic moiety is selected from pyridinium core surface-active cationic molecules such as cetylpyridinium chloride, laurylpyridinium chloride, etc.; from chlorhexidines such as chlorhexidine, its diacetate, chlorhexidine digluconate, chlorhexidine dihydrochloride; from monalkyl quaternary ammonium compounds (quats) such as benzalkonium chloride, cetalkonium chloride and bromide, lauralkonium chloride and bromide, soytrimonium chloride, PEG-5 stearyl ammonium lactate; from dialkyl quaternary ammonium compounds (diquats) such as dilauryl dimonium chloride, dicetyl dimonium chloride and bromide, dequalinium chloride, soyamido propyl benzyldimonium chloride, quaterniums such as quaternium 15 and polyquaterniums, etc; amine fluorides, from cationic polysaccharides, such as chitosan and its derivatives; from cationic polypeptides, such as poly L-lysine, poly D-lysine, lysozyme.

In especially preferred embodiments of the present invention said amphipathic cationic moiety is selected from cetylpyridinium chloride, a chlorhexidine compound, chitosan, chitin derivatives, poly L-lysine and lysozyme.

The invention also provides a method for enhancing microbial adhesion at an oil-water interface comprising admixing an aqueous microbial suspension and oil in the presence of an amphipathic cationic moiety.

In U.S. Pat. No. 4,525,342, Weiss et al. have described an essentially detergent free mouthwash based on a combination of an oily phase and an aqueous one. This composition must be marketed in a two-compartment squirt bottle, and the user swishes the two phases in his mouth in order to attain the desired effect. The composition is based on the attachment of amphipathic substances to the oil droplets during the swishing action, thus coating the oil droplets. The presence of detergents is reported to be deleterious in said patent. Various deleterious physiological effects have been reported regarding the use of detergents in the oral cavity. It has been reported that the presence of detergents prevents, or at least decreases adhesion of microorganisms to oil droplets as is taught, e.g. by the statement: "The aqueous bacterial suspension must be free of surfactants, which inhibit the assay" (M. Rosenberg, 1984. Bacterial Adherence to Hydrocarbons: A Useful Technique for Studying Cell Surface Hydrophobicity. FEMS Microbiology Letters 22, 289–295). In a recent review on hydrophobic interactions and adhesion, the authors write: "Our appreciation of the extent to which hydrophobic interactions mediate various bacterial adhesion phenomena could be greatly augmented by including agents that interfere with hydrophobic interactions (e.g., surfactants, chaotrophic agents) in adhesion assays (M. Rosenberg and S. Kjellerberg, 1986, Hydrophobic Interactions: Role in Bacterial Adhesion. Advances in Microbial Ecology 9, 353–393). Moreover, in a previous study which did examine the effect of some cationic amphipathic antibacterial agents on adhesion of relatively non-hydrophobic *Escherichia coli* strains to xylene, the cells were exposed to the cationic agents, but the cationic agents were subsequently removed by washing the cell pellet prior to addition of the xylene, presumably to avoid inhibition of the adhesion in the presence of the cationic agents (B. M. A. El-Falana, D. T. Rogers, A. D. Russell and J. R. Furr. 1985 Effect of Some Antibacterial Agents on the Hydrophobicity of Wild-Type and Envelope Mutant of *Escherichia coli*. Current Microbiology 12, 187–190). Similarly, chlorhexidine, an amphipathic, surface-active cationic agent commonly incorporated into mouthwashes has been shown in many studies to inhibit microbial adhesion to surfaces. For example, J. McCourtie, T. W. MacFarlane and L. P. Samaranayake (Effect of saliva and serum on the adherence of Candida species to chlorhexidine-treated denture acrylic, J. Med. Microbiology, 21:209–213, 1986) showed that treatment of saliva- or serum-coated acrylic with chlorhexidine gluconate reduced adherence by between 19 and 86%.

Moreover, whereas salts such as sodium chloride have been generally considered to enhance microbial adhesion to surfaces, it has now been found that the presence of inorganic cations, such. as sodium and magnesium cations, inhibit the stimulation of adhesion brought about by cationic moieties such as cetylpyridinium, chlorhexidine, chitosan, poly L-lysine, poly D-lysine and lysozyme.

The main use of the compositions is in the form of mouthwashes, which effectively remove a large percentage of microorganisms, debris and other odor-causing materials from the surface of teeth and from the oral cavity. Thus especially preferred embodiments of the present invention relate to a mouthwash as defined above comprising about 0.003 to about 0.5 w/w of an amphipathic cationic moiety in an effective amount to enable the formation of said temporary oil-in-water emulsion which emulsion breaks down and separates within a period of about 10 seconds to thirty minutes of the formation thereof.

The novel compositions comprise, in combination, an organic water-immiscible phase and an aqueous phase, and a small quantity of an amphipatic cationic moiety, which is adequate to form upon vigorous mixing an emulsion of brief life-time. In addition, the composition may comprise additional cationic agent or agents which enhance adhesion to oil droplets, as shall be illustrated later. Optimally, the composition should be relatively free from interfering cations, such as sodium, potassium and magnesium and therefore preferably contain only up to 0.3% of inorganic salts.

In use, the two phases are mixed by shaking, and an emulsion is formed which is used for swishing in the mouth, and which has a limited life time, of the duration of about 10 seconds to about 30 minutes. A small amount of amine fluoride which tends to stabilize the emulsion for a brief period of time and has other beneficial (e.g. anticaries, antibacterial) effects may also be added.

There may also be incorporated certain additives such as fragrances, colors and the like.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The following experimental results illustrate the invention, both in regard to the specific formulations and also as regards the mechanism of action of the emulsions of the present invention as regards removal of dental plaque and adhering bacterial and other microorganisms.

The mouthwash compositions of the invention preferably comprise a small quantity of an amphipatic cationic moiety which is preferably a surface-active agent which is able to form an emulsion of limited life time. The emulsion ought to be formed upon shaking of the container which contains the two separate phases, and it should preferably remain in emulsion form for at least about 20 seconds. Experiments have shown that compositions of the invention form temporary emulsions which separate after a period of about 10 seconds to 10 minutes.

We have found the unexpected result that small amounts of cationic surface-active agents promote, rather than inhibit, adhesion of bacteria and oral debris, to oil droplets. We have also found the surprising and unexpected results that sodium and magnesium chloride inhibit, rather than enhance, microbial adhesion in the presence of such cationic agents as (cetylpyridinium chloride, chlorhexidine digluconate and chitosan.

The following experiments demonstrate the ability of the cationic surfactant, cetylpyridinium chloride, to enhance microbial adhesion to oil droplets in various experiments. In one experiment *Acinetobacter calcoaceticus* RAG-1 (ATCC 31012) cells were grown overnight with vigorous shaking at 30 C in brain heart infusion broth. The cells were harvested by centrifugation and washed twice in 0.2% saline. The cells were then suspended in 0.2% saline to a corrected optical density of about 15 at 400 nm (1 cm light path). To 1.2 ml of suspended bacteria in 4 ml square disposable polystyrene cuvettes were added the following: 0.16 ml of 0.5% detergent in water (or water for control) and 0.24 ml water. Following brief mixing, 0.2 ml of oil was added (vs. controls with no oil added) and the mixtures vortexed vigorously for 2 min. Following about thirty minutes, the corrected turbidity of the lower aqueous phase was measured at 400 nm. Adhesion is calculated as the percent drop in turbidity following the mixing procedure. The results are summarized in the following Table.

TABLE 1

Adhesion RAG-1 to various oils in the presence of cetylpyridinium chloride

| Additions | Percent adhesion to: | | |
|---|---|---|---|
| | n-nexadecane | mineral oil 50 | soybean oil |
| Cetylpyridinium chloride | 83 | 80 | 47 |
| None | 27 | 5 | 32 |
| Sodium dodecyl sulphate | 0 | 0 | 0 |
| Tween 20 | 0 | 0 | 0 |

As can be seen from the above Table, in each case, cetylpyridinium chloride greatly enhanced bacterial adhesion to the oil droplets. This phenomenon was also observed microscopically. Enhanced adhesion was not observed for non-cationic surface-active agents: adhesion to all three test oils in the presence of the anionic sodium lauryl sulphate or the nonionic Tween 20, added at the same concentration as the cetylpyridinium chloride (w/v), was 0%. Morever, the enhanced adhesion can be shown also for microbial cells other than RAG-1 which have little or no affinity for oil droplets. For example, the adhesion of *Escherichia coli* CSH 57 to hexadecane could be increased from 0 to 98% when 0.08% cetylpyridinium chloride was present; adhesion of the yeast *Candida alpicans* rose from 20 to 100% in the presence of 0.16% chlorhexidine digluconate. Adhesion of *Acinetobacter calcoaceticus* MR-481 rose from 0 to 97% in the presence of 0.18% of cetylpyridinium chloride.

In another experiment, a volunteer swished his mouth with 0.2% saline solution (10 ml) for thirty seconds. To 1 ml of the expectorate were ad ed 0.18 ml of 0.5% cetylpyridinium chloride (water in the case of the control) and 0.44 mm 0.2% saline. Mineral oil 50 (0.2 ml) was then added and the mixtures vortexed for 2 minutes. Following phase separation, the mixtures were examined. Whereas the turbidity of the expectorate was greatly reduced in the presence of cetylpyridinium chloride, presumably due to adsorption of bacteria and debris to the oil droplets, in the absence of this detergent, no increase in turbidity was observed.

The ability of another cationic surface-active agent, chlorhexidine digluconate, to enhance microbial adhesions to oil droplets is shown in the following experiment. *Actnetobacter calcoaceticus* RAG-1 (ATCC 31012) cells were grown overnight with vigorous shaking at 30 C in brain heart infusion broth. The cells were harvested, washed by centrifugation, and suspended in 0.2% saline to a corrected optidal density of ca. 18 at 0 nm (1 cm light path). To 1.2 ml of suspended bacteria in 4 ml square disposable polystyrene cuvettes were added the following: 0.16 ml of 0.5% chlorhexidine digluconate in water (or water for control) and 0.24 ml water. To each cuvette 0.2 ml of oil was added (vs. control with no oil added) and the mixtures vortexed vigorously for 2 min. After about thirty minutes, the turbidity of the lower aqueous phase was measured at 400 nm and corrected for non-linearity by a standard curve. Adhesion is calculated as the percent drop in corrected turbidity following the mixing procedure. The results are summarized in the following Table.

TABLE 2

Adhesions of RAG-1 to various oils in the presence of chlorhexidine digluconate

| | Percent adhesion to | | | |
|---|---|---|---|---|
| Additions: | n-hexa-decane | isohexa-decane | Sigma* soybean oil | Commerical soybean oil |
| Chlorhexidine digluconate | 95 | 94 | 90 | 89 |
| None | 50 | 66 | 54 | 49 |

*St. Louis, Mo.

As can be seen from the above Table, in each case chlorhexidine digluconate greatly enhances bacterial adhesion to the oil droplets. Moreover, the enhanced adhesion can be shown also for microbial cells other than RAG-1 which have little or no affinity for oil droplets. For example, the adhesion of *Escherichia coli* CSH 57 to hexadecane could be increased from 0 to 98% when 0.1% chlorhexidine digluconate was present.

Adhesion to oil droplets may also be enhanced by polymeric cationic agents, such as chitosan. For example, the adhesion of *Escherichia coli* CSH 57 to hexadecane could be increased from 0 to 97% when 0.015% chitosan was present; adhesion of the yeast *Candida albicans* rose from 20 to 95% in the presence of 0.025% chitosan. Adhesion of *Acinetobacter calcoaceticus* MR-481 rose from 0 to 99% in the presence of 0.019% of chitosan.

The compositions of the invention are suitable for a variety of applications. As a two-phase mouthwash, containing an aqueous phase and an oil phase, the presence of adhesion-enhancing cationic agent (or combination thereof) could remove and bind high levels of oral microorganisms and debris.

The enhanced Adhesion of RAG-1 cells to oils in the presence of cationic surfactants similarly teaches the use of cationic surface-active agents to enhance microbial adhesion to oils for commercial purposes, such as immobilization of cells onto oil droplets, or of cells, cell walls, and the like for enhanced adhesion to adjuvant oils in the vaccination field.

In general, salts such as sodium chloride, magnesium chloride and various phosphates, enhance adhesion of microorganisms to surface by countering the net negative charges which generally exist on cell surfaces, and often on substrata surfaces. Weiss et al. include in their U.S. Pat. No. 4,525,342, a requirement for salt. However, as stated, it has now been found that the enhancement of microbial adhesion to oils observed in the presence of cetylpyridinium chloride, chlorhexidine gluconate and chitosan is inhibited by sodium chloride and magnesium chloride.

For example, adhesion of *C. albicans* to hexadecane in the presence of 0.16% cetyl pyridinium chloride fell from 100% to 18% when 0.8% NaCl was present.

In order to obtain a picture as to the efficacy of the compositions of the invention for oral use these were compared with existing mouthwashes as regards their ability to remove a given bacterial film from a solid surface.

There were used a number of commercial products and these were compared with the preparation of the invention defined below as ODEX-35. The following describes and illustrates in detail specific features of the invention:

EXAMPLE ODEX-35

Aqueous phase:

| | |
|---|---|
| sodium chloride | 0.2% w/w |
| sodium saccharin | 0.05% w/w |
| FD&C Blue No. 1 | 0.0001% w/w |
| cetyl pyridinium chloride | 0.03% w/w |
| water | to 100% |

Oil phase

| | |
|---|---|
| soybean oil | 35.0% w/w |
| essential oil (mint) | 1.5% w/w |

This type of formulation has several advantages. First, the presence of cetylpyridinium chloride results in adsorption of much higher levels of bacterial and oral debris, than when it is absent. Second, the mixture can be presented in a single, regular container, e.g. bottle, obviating the need for a double compartment, double squirt bottle. The user simply shakes for several seconds, the amount of cetylpyridinium chloride is sufficient to provide an emulsion with limited stability which enables the user to pour the desired quantity of mixture and use it directly to swish and gargle. An added advantage of the formulation is that the cetylpyridinium chloride enhances the dye binding capacity of the bacteria and debris so that they are clearly colored blue by the dye, facilitating their observation. Moreover, the dye and cetylpyridinium chloride may act together in a synergistic fashion as antibacterial agents.

In one experiment, the formulation was mixed, and 10 ml immediately poured into a small cup. Volunteers swished and gargled with the mixture for a thirty second period. Following swishing, the mixture was expectorated into test tubes. It was clearly observed in all cases that the oral bacteria and debris, dyed blue, rose together with the yellow oil droplets, creating a green upper oil:in:water emulsion which was stable for hours. Bacteria, and bacteria-coated epithelial cells were microscopically observed adhering to the oil droplets. The aqueous phase lost its blue color, presumably due to the binding of the dye to the great quantities of bacteria and debris removed onto the oil droplets during the mixing procedure. A drop in the level of bad breath of the volunteers was evident for hours following the swishing procedure. Moreover, volunteers reported a long lasting fresh feeling in their mouths, and did not report any oily taste, despite the high level of oil in the preparation. These observations could not be reproduced if either the oil phase, or the cationic surface-active agent were absent.

It should be emphasized that the compositions of the invention also have a wide range of uses in enhanced desorption of microorganisms for host, industrial and environmental surfaces onto oil droplets. To illustrate this point, we have succeeded in demonstrating that the above formulation is highly effective in removing adsorbed bacteria from a model surface, i.e. polystyrene, as described in the following experiment.

One ml of a very turbid suspension of RAG-1 cells in 150 mM phosphate buffer was added to a polystyrene cuvette (4 ml capacity). Following 1 minute vortexing, the RAG-1 cells were poured off, leaving a film of adherent cells. The cuvettes were washed briefly with tap water. To each cuvette, 1 ml of mouthwash (when indicated, diluted according to instructions) or water (control) were added and the cuvettes vortexed for 2 minutes. The mouthwash was poured off, 1 ml fresh mouthwash was added, and the cuvettes again vortexed for 2 minutes. The mouthwash was poured of, and the remaining bacterial film stained by adding Gentian Violet to the cuvettes, followed by washing to remove excess stain. The amount of bacterial film was ascertained by measuring the optical absorbance (585 nm) of the dried cuvettes from both sides in a Uvikon spectophotometer. The results are presented in Table 3.

From the following Table it can be seen that among the commercial mouthwashes tested, several (Eludril, P. F. Medicament, 125, rue de la Faisanderie, Paris, France; Tayadent, Taya Ltd., Petach Tiqua, Israel and Act®, Johnson & Johnson, New Brunswick, N.J. 08903) were less able than water to desorb the bacterial film. Menthol Chloraseptic® (Norwich Eaton Pharmaceuticals, Inc., Norwich, N.Y. 13815) and Veadent® (Glaxo, under licence from Vipont Laboratories Inc., Ft. Collins, U.S.A.)desorbed less than 10% of the adherent bacteria. Cepadont removed 29% of the film. Only ODEX-35 removed the large majority (87%) of the bacterial film. Moreover, ODEX-35 without the oil phase was relatively ineffective (26%) as compared to both phases together (87%).

TABLE 3

| Mouthwash | $OD_{585\,nm}$ (mean) | Percent removal relative to water control |
|---|---|---|
| Control (water | 0.300 | — |
| Eludril | 0.625 | — |
| Tayadent | 0.376 | — |
| Act (green) | 0.344 | — |
| Menthol Chloraseptic | 0.288 | 4 |
| Veadent | 0.281 | 6 |
| Cepadont | 0.213 | 29 |
| ODEX-35, aqueous phase only | 0.223 | 26 |
| ODEX-35 | 0.039 | 87 |

In order to further test compositions of the kind described above for use as mouthwashes, several in vivo tests were undertaken. In one of these, various compositions were prepared and swished for two thirty second periods by a volunteer at bedtime. The following morning, the volunteer swished with ten ml of sterile milk, and 3 ml of the expectorate was mixed in a test tube with 0.12 ml of 0.1% methylene blue. The test tube was allowed to stand at room temperature and the time required for the bottom of the test tube to turn white was observed. It has been previously shown that the time required for a color change from blue to white at the bottom of the test tube correlates highly with microbial counts, thus a table was used to convert the time for color change into relative microbial counts. The results are presented in Table 4, together with the time required for the color change, and the percentage of microorganisms remaining, as compared to a no-mouthwash control. Several of the compositions could not be mixed or were unattractive (samples 3 and 14) and were not tested in the mouth. Others (samples 16 and 23A) were tried several times.

TABLE 4

| | Ingredients (% w/w) | | | | | | | | | | | |
|---|---|---|---|---|---|---|---|---|---|---|---|---|
| Sample Number | Soybean oil | Mineral oil | Peppermint oil | Cetyl pyridinium chloride | Sodium lauryl sulphate | Chlorhexidine digluconate | Sodium saccharin | Xylitol | Aspartame | Sodium chloride | Ethanol (absolute) | Tween 20 |
| 1 | 35 | — | 1.5 | 0.05 | — | — | 0.05 | — | — | — | — | — |
| 2 | 35 | — | 1.5 | 0.025 | — | — | 0.05 | — | — | — | — | — |
| 3 | 35 | — | 1.5 | — | — | 0.04 | 0.05 | — | — | — | — | — |
| 4 | 35 | — | 1.5 | 0.025 | — | 0.04 | 0.05 | — | — | — | — | — |
| 5 | 35 | — | 1.5 | — | — | 0.2 | — | 5 | — | — | — | — |
| 6 | 35 | — | 1.5 | — | — | 0.2 | — | — | 0.1 | — | — | — |
| 6 | 35 | — | 1.5 | — | — | 0.2 | — | — | 0.1 | — | — | — |
| 12 | 35 | — | 1.5 | — | — | 0.1 | — | — | 0.1 | — | — | — |
| 13 | 35 | — | 1.5 | — | — | 0.05 | — | — | 0.1 | — | — | — |
| 14 | 35 | — | 1.5 | — | — | 0.025 | — | — | 0.1 | — | — | — |
| 15 | 35 | — | 1.5 | 0.05 | — | 0.1 | — | — | 0.1 | — | — | — |
| 16 | 35 | — | 1.5 | 0.05 | — | 0.05 | — | — | 0.1 | — | — | — |
| 16 | 35 | — | 1.5 | 0.05 | — | 0.05 | — | — | 0.1 | — | — | — |
| 22A | 25 | — | 1.5 | 0.05 | — | 0.05 | — | — | 0.1 | — | — | — |
| 23A | 15 | — | 1.5 | 0.05 | — | 0.05 | — | — | 0.1 | — | — | — |
| 23A | 15 | — | 1.5 | 0.05 | — | 0.05 | — | — | 0.1 | — | — | — |
| 24A | 5 | — | 1.5 | 0.05 | — | 0.05 | — | — | 0.1 | — | — | — |
| 25 | — | — | 0.1 | — | — | 0.1 | — | — | 0.1 | — | — | 0.4 |
| 26 | — | — | 0.1 | 0.05 | — | 0.05 | — | — | 0.1 | — | — | 0.4 |
| 31 | — | 15.0 | 1.5 | 0.05 | — | 0.05 | — | — | 0.1 | — | — | — |
| 32 | 5 | — | 0.75 | 0.05 | — | 0.05 | — | — | 0.1 | — | — | — |
| 34 | 33 | — | 1.5 | — | 0.10 | — | — | — | 0.1 | — | — | — |
| 35 | 35 | — | 1.5 | 0.05 | — | 0.05 | — | — | — | 0.2 | — | — |
| 36 | 35 | — | 1.5 | 0.05 | — | 0.05 | — | — | — | — | 16.0 | — |

TABLE 4-continued

| | Ingredients (% w/w) | | | Results: | |
|---|---|---|---|---|---|
| Sample Number | FD&C Blue No. 1 (Food Blue 2: CI 42090) | | Water | Time for color change | % residual micro-organism |
| 1 | 0.00002 | to | 100% | 30' | 36.0 |
| 2 | 0.00002 | to | 100% | 14' | 61.0 |
| 3 | 0.00002 | to | 100% | — | — |
| 4 | 0.00002 | to | 100% | 10' | 77.0 |
| 5 | 0.00002 | to | 100% | >80' | <18.0 |
| 6 | 0.00002 | to | 100% | 90 | 17.0 |
| 6 | 0.00002 | to | 100% | 420' | 6.0 |
| 12 | 0.00002 | to | 100% | >100' | <15.0 |
| 13 | 0.00002 | to | 100% | 35' | 32.0 |
| 14 | 0.00002 | to | 100% | — | — |
| 15 | 0.00002 | to | 100% | >124' | 13.0 |
| 16 | 0.00002 | to | 100% | >160' | 11.0 |
| 16 | 0.00002 | to | 100% | >120' | <14.0 |
| 22A | 0.00002 | to | 100% | >142' | <12.0 |
| 23A | 0.00002 | to | 100% | >264' | <8.0 |
| 23A | 0.00002 | to | 100% | >226' | <9.0 |
| 24A | 0.00002 | to | 100% | 129' | 13.0 |
| 25 | 0.00002 | to | 100% | <30' | >36.0 |
| 26 | 0.00002 | to | 100% | 32' | 34.0 |
| 31 | — | to | 100% | 90' | 17.0 |
| 32 | 0.00002 | to | 100% | 119' | <14.0 |
| 34 | 0.00002 | to | 100% | 31' | 36.0 |
| 35 | 0.00002 | to | 100% | 35' | 32.0 |
| 36 | 0.00002 | to | 100% | 19' | 49.0 |

It is clear from Table 4 that a positive interaction exists between cetylpyridinium chloride and chlorhexidine. Thus, whereas sample 1 containing only cetylpyridinium chloride (0.05%) as cationic agent and sample 13 containing only chlorhexidine digluconate (0.05%) as cationic agent left a high percentage of residual microorganisms in the mouth (over 30%), a combination of 0.05% cetylpyridinium chloride and 0.05% chlorhexidine (sample 16) was highly effective, leaving less than 14% residual microorganisms in one instance, and 11% in another. Moreover, the cetylpyridinium chloride has a better emulsifying ability, whereas chlorhexidine digluconate has better antibacterial activity. Thus, the combination of both together with the oil is highly effective in obtaining a composition which can be effectively emulsified by shaking for a brief period, combined with potent antibacterial ability. It should be noted that compositions containing from 5–35% (w/w) of soybean oil, cetylpyridinium chloride, and chlorhexidine were highly effective (samples 15,16, 22A–24A). Another advantage of the two-phase oil:water combination is that moieties which generally require emulsification in regular mouthwashes can be added to the oil phase. For example, in order to introduce peppermint oil into the aqueous phase, it must be solubilized e.g. with Tween. This causes a great reduction in activity of the formula, by inactivating the cations (e.g. chlorhexidine) present (see for example the poor performance of samples 25 and 26, even though antibacterial cations are present).

Thus, when antibacterial cations such as chorhexidine are present in the aqueous phase, it is preferable to add the oil-soluble components to the oil phase. Such components include flavors, antioxidants (e.g. Vitamin E, BHA, BHTA), and essential oils which have antibacterial activity, e.g. eucalyptis oil, cinnamon oil.

On the other hand, samples in which the essential oil (peppermint) was solubilized in the aqueous phase using Tween 20 (samples 25 and 26) were not effective, even though either 0.1% chlorhexidine (sample 25) or a combination of 0.05% of both cetylpyridinium chloride and chlorhexidine (sample 26) were present.

Bad breath is known to be chiefly due to microbial activity in the oral cavity. Sample 23A was tested against a leading commercial mouthwash (Listermint, Warner-Lambert Health Care Ltd., Eastleigh, Hants, England) for its ability to reduce bad breath levels, as determined by oral sulphide levels, using a sulphide monitor, (Interscan Model 1170, Interscan Ltd., Chatsworth, Calif.). One-quarter inch plastic straws are inserted into the sample inlet and the volunteer allows the end of the straw to enter the oral cavity, and breathes through his nose. The peak and steady-state value are recorded in parts per billion sulphide equivalents. Volunteers swished with either mouthwash for two thirty second periods at bedtime and tested peak and steady-state sulphide levels immediately upon awakening. Sample 23A reduced peak levels by 74%, and steady-state levels by 70%, as compared to no-mouthwash controls; in contrast, Listermint reduced peak levels by 51% and steady state levels by 45% as compared to no-mouthwash controls. Moreover, in a comparison of the ability of sample 23A to remove bound microorganisms from a solid surface, in an experiment analogous to that described in Table 3, sample 23A was superior to a wide variety of commercial mouthwashes in its ability to desorb bound cells.

As an additional example, we have tested formulations whose oil phase contains a combination of olive oil, peppermint oil and eucalyptus oil. One formulation, designated ODEX, has the following composition:

Aqueous Phase:

| | |
|---|---|
| cetylpyridinium chloride | 0.05% (w/w) |
| aspartame | 0.1% (w/w) |
| FD&C blue no. 1 | 0.1% of a 1% w/w aqueous solution |
| water | 84.75% (w/w) |

Oil Phase:

| | |
|---|---|
| olive oil | 13.50% (w/w) |
| peppermint oil | 1.00% (w/w) |
| eucalyptus oil | 0.5% (w/w) |

Another formulation, designated ODEX+ has the following composition:

Aqueous Phase:

| | |
|---|---|
| cetylpyridinium chloride | 0.05% (w/w) |
| chlorhexidine digluconate | 0.05% (w/w) |
| aspartame | 0.1% (w/w) |
| FD&C blue no. 1 | 0.1% of a 1% w/w aqueous solution |
| water | 84.70% (w/w) |

Oil Phase:

| | |
|---|---|
| olive oil | 13.50% (w/w) |
| peppermint oil | 1.00% (w/w) |
| eucalyptus oil | 0.5% (w/w) |

The ability of these formulations to desorb microorganisms from polystyrene was tested as described in reference to Table 3. ODEX and ODEX+ removed 98% and 92%, respectively, of the bound RAG-1 bacteria.

Moreover, ODEX was tested in its ability to reduce bad breath, as compared to the following controls: (i) a commercial mouthrinse, Cepadont; (ii) a control in which the oil phase was entirely omitted; (iii) a control in which the olive and peppermint oil were omitted, and the eucalyptus oil solubilized in 6% Tween 20; and (iv) no mouthrinsing control. Peak morning odor was measured using the Interscan 1170 sulphide analyzer. Two volunteers rinsed, prior to bedtime, for two consecutive 30 second periods. Immediately upon awakening, peak sulphide was measured. The results are summed up in Table 5 below:

TABLE 5

Overnight Effect of ODEX on Bad Breath

| | Parts per billion sulphide equivalents | |
|---|---|---|
| FORMULATION TESTED | Volunteer 1 | Volunteer 2 |
| ODEX | 25 | 20 |
| (i) Cepadont | 140 | 70 |
| (ii) No oil phase | 70 | 40 |
| (iii) Solubilized eucalyptus oil | 60 | — |
| (iv) No mouthrinsing | 117 | 150 |

These data show that the combination of aqueous phase and non-emulsified oil phase containing eucalyptus oil was more effective than any of the controls.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A composition for desorbing bacteria from solid surfaces and from living tissues, comprising:
    a) about 50 to about 97% w/w of an aqueous phase;
    b) about 3 to about 50% w/w of a water immiscible oily phase; and
    c) about 0.003 to about 2.0% w/w of an amphipathic cationic moiety in an effective amount to enable the formation of a temporary oil-in-water emulsion which emulsion breaks down and separates within a period of about 10 seconds to thirty minutes of the formation thereof,
wherein said composition is in the form of a two-phase preparation not requiring physical separation, and which upon shaking forms a temporary oil-in-water emulsion of limited lifetime.

2. A composition for desorbing bacteria from solid surfaces and from living tissues, according to claim 1 wherein said amphipathic cationic moiety is selected from the group consisting of pyridinium core surface-active cationic molecules, chlorhexidines, monalkyl quaternary ammonium compounds, dialkyl quaternary ammonium compounds, quaterniums and polyquaterniums, amine fluorides, cationic polysaccharides, and cationic polypeptides.

3. A composition for desorbing bacteria from solid surfaces and from living tissues, according to claim 1 wherein said amphipathic cationic moiety is selected from the group consisting of cetylpyridinium chloride, a chlorhexidine compound, chitosan, chitin derivatives, poly L-lysine and lysozyme.

4. A composition according to claim 1, wherein the oily phase is selected from the group consisting of olive oil, corn oil, coconut oil, soybean oil, safflower oil, octane, decane, tetradecane, hexadecane, white mineral oil and a mixture of two or more thereof.

5. A composition according to claim 1 wherein said amphipathic cationic moiety is a chlorhexidine compound.

6. A composition according to claim 1 wherein said amphipathic cationic moiety is chitosan.

7. A mouthwash according to claim 1 comprising about 0.003 to about 0.5 w/w of an amphipathic cationic moiety in an effective amount to enable the formation of said temporary oil-in-water emulsion which emulsion breaks down and separates within a period of about 10 seconds to thirty minutes of the formation thereof.

8. A composition according to claim 1 containing up to 0.3% of inorganic salts, selected from the group consisting of phosphate, sodium or magnesium chloride and fluorides.

9. A composition according to claim 1 which contains about 0.005 to 0.5% cetylpyridinium chloride.

10. A composition according to claim 1 which contains about 0.005 to 0.5% cetylpyridinium chloride and about 0.005 to 0.5% of a chlorhexidine compound.

11. A composition according to claim 1 further comprising a pharmaceutically acceptable dye which binds to microorganisms and debris.

12. A method of removing microorganisms from a surface comprising the steps of:

a) shaking a two-phase mixture including an aqueous phase, a water-immiscible oil phase, and an amphipathic cationic moiety in sufficient amount to form, upon shaking, a temporary oil-in-water emulsion which breaks down and separates within a period of from about ten seconds to thirty minutes; and b) applying said temporary oil-in-water emulsion to said surface.

13. The composition according to claim 1, wherein said water immiscible oily phase is selected from the group consisting of a vegetable oil, a mineral oil, a pharmaceutically acceptable aliphatic hydrocarbon, and a mixture thereof.

* * * * *

UNITED STATES PATENT AND TRADEMARK OFFICE
Certificate

Patent No. 6,465,521 B1            Patented: October 15, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Melvyn Rosenberg, Ramat-Gan, IL; and Dr. Yoel Konis, Hadera, Israel.

Signed and Sealed this Thirtieth Day of March 2004.

SREENI PADMANABHAN
*Supervisory Patent Examiner*
Art Unit 1617